United States Patent
Urban

Patent Number: 5,719,286
Date of Patent: Feb. 17, 1998

[54] PROCESS AND INTERMEDIATES FOR BIS-AZA-BICYCLIC ANXIOLYTIC AGENTS

[75] Inventor: Frank John Urban, Waterford, Conn.

[73] Assignee: Pfizer Inc., New York, N.Y.

[21] Appl. No.: 338,549

[22] PCT Filed: Feb. 16, 1993

[86] PCT No.: PCT/US93/01208

§ 371 Date: Dec. 12, 1994

§ 102(e) Date: Dec. 12, 1994

[87] PCT Pub. No.: WO93/25552

PCT Pub. Date: Dec. 23, 1993

[51] Int. Cl.[6] .......... C07D 471/04; C07D 487/04
[52] U.S. Cl. .......... 544/349; 544/295; 544/229
[58] Field of Search .......... 544/230, 349, 544/242, 335, 295, 229; 514/249, 254

[56] References Cited

U.S. PATENT DOCUMENTS

| | | |
|---|---|---|
| 4,956,368 | 9/1990 | Cipollina et al. .......... 514/254 |
| 5,122,525 | 6/1992 | Bright et al. .......... 514/249 |
| 5,157,034 | 10/1992 | Bright et al. .......... 514/249 |

*Primary Examiner*—John M. Ford
*Attorney, Agent, or Firm*—Peter C. Richardson; Paul H. Ginsburg; Bryan C. Zielinski

[57] ABSTRACT

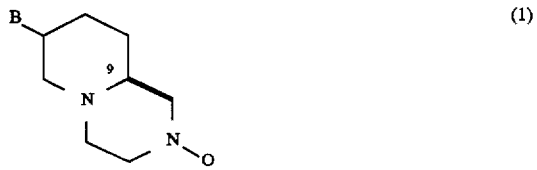

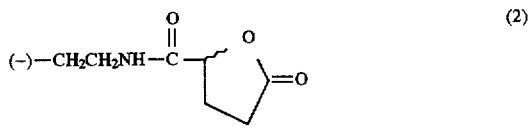

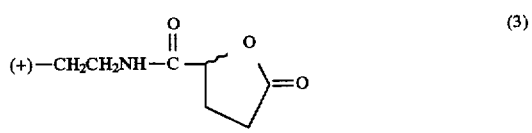

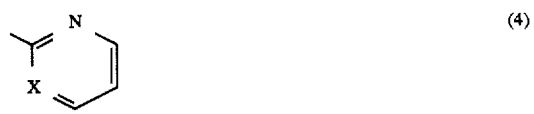

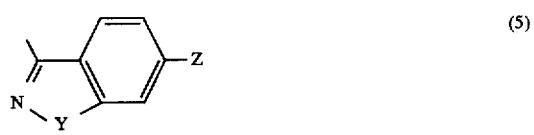

Optically pure intermediates of formula (1) wherein the substituent B is either cis or trans to the $C_{9a}$–$C_1$ bond and is selected from the group consisting of —$CH_2OH$, —CHO, —$CH_2OSO_2R$, —$CH_2CN$, —CH(OH)$CH_2NO_2$, —CH=CH—$NO_2$, (2) and (3), C is selected from the group consisting of —H, (4), (5), and a nitrogen protecting group which is removable by hydrogenation or acid treatment; and wherein R is ($C_1$–$C_8$) alkyl, phenyl or alkyl substituted phenyl; X is N or CH; Y is O or S and Z is H or Cl; for the synthesis of octahydro-1H-pyrido(1,2-a)pyrazinyl ethyl carboxamide anxiolytic agents.

10 Claims, No Drawings

5,719,286

1

PROCESS AND INTERMEDIATES FOR BIS-AZA-BICYCLIC ANXIOLYTIC AGENTS

This is a national stage application, filed pursuant to 35 U.S.C. §371, of PCT international application number PCT/US93/01208, filed Nov. 16, 1993.

BACKGROUND OF THE INVENTION

The present invention is directed to an improved process for intermediates useful for the synthesis of the anxiolytic agents represented by structures I and II below as well as new anxiolytic agents and intermediate compounds. Commonly owned European patent application A 038,217 filed Jan. 12, 1990 and U.S. patent applications Ser. Nos. 661, 791, filed Feb. 27, 1991 (PCT/US91/08378, filed Nov. 18, 1991); 661,726, filed Feb. 27, 1991; and 661,730, filed Feb. 27, 1991 (PCT/US91/08400, filed Nov. 19, 1991) described the synthesis of Compound I and related intermediates in Scheme A shown below.

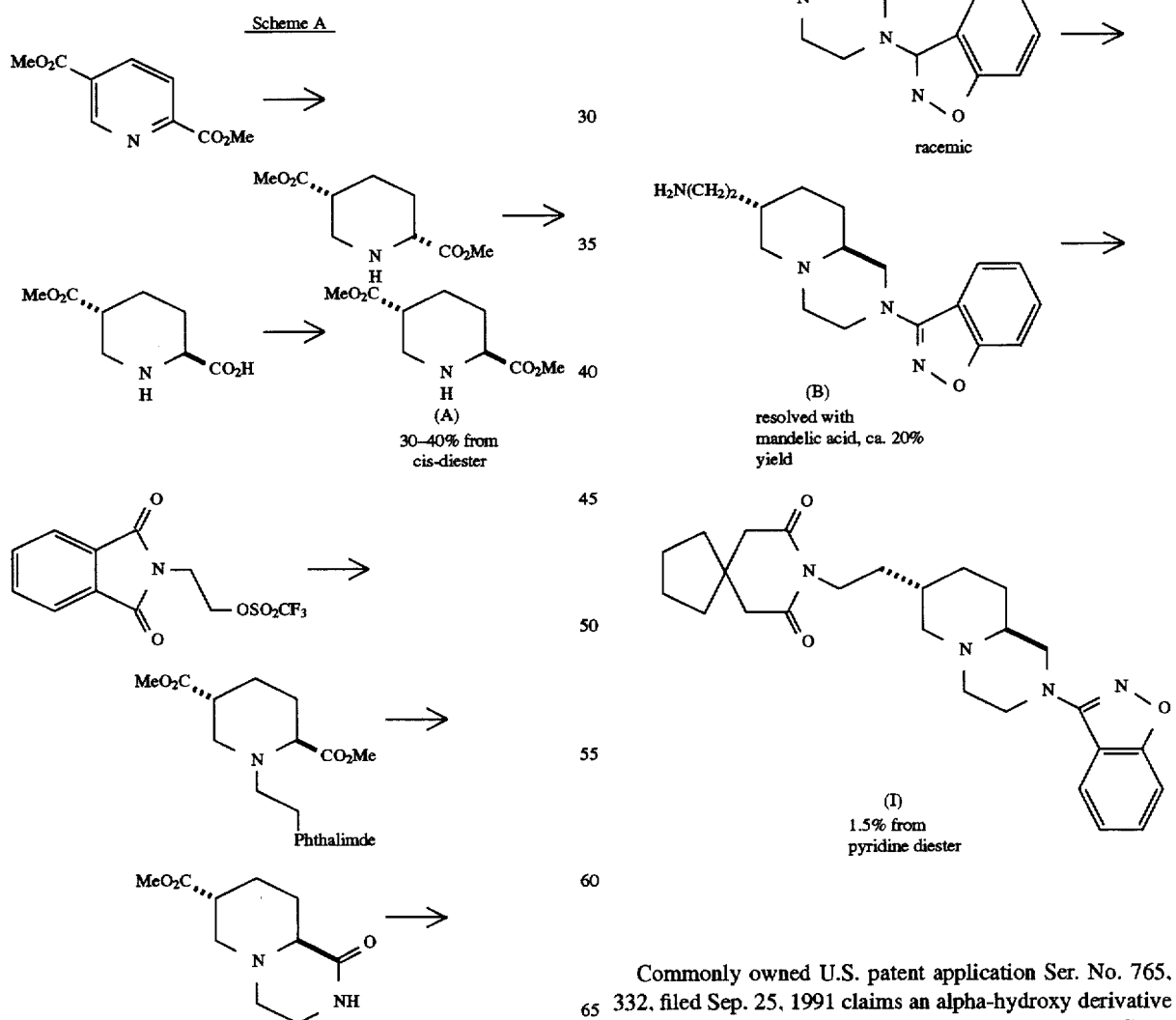

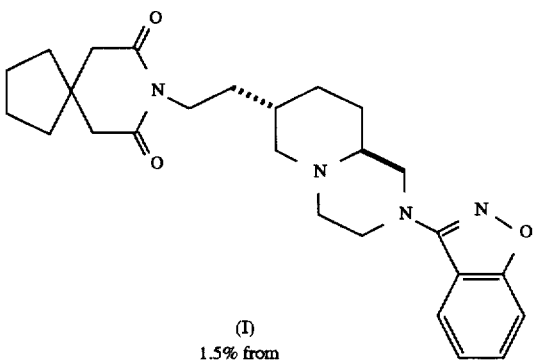

Commonly owned U.S. patent application Ser. No. 765, 332, filed Sep. 25, 1991 claims an alpha-hydroxy derivative of Compound I with the structure shown below as Compound II.

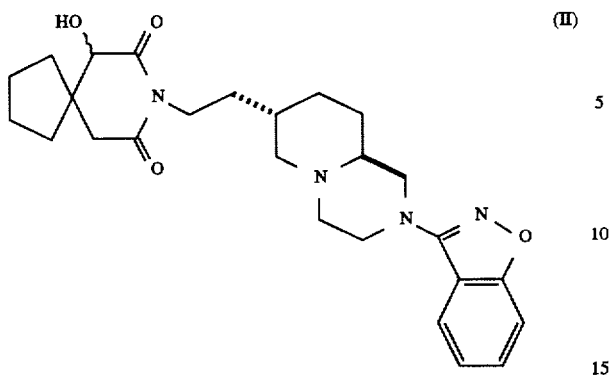

(II)

U.S. Pat. No. 4,956,368 teaches that compounds hydroxylated at C-6 of the azaspirodecanedione portion of a molecule may rearrange to produce an oxaspirononanone of the type:

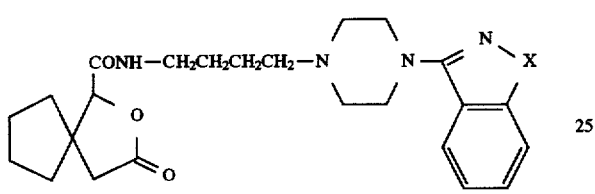

The text of commonly owned U.S. patent application Ser. Nos. 661,791; 661,726; 661,730; and 765,332 is herein incorporated by reference.

SUMMARY OF THE INVENTION

The present invention is directed toward an improved process for the synthesis of anxiolytic agents of Compounds I and II above and intermediate compounds used in this synthesis. The new synthesis also provides a facile synthesis of new anxiolytic compounds of formula III below.

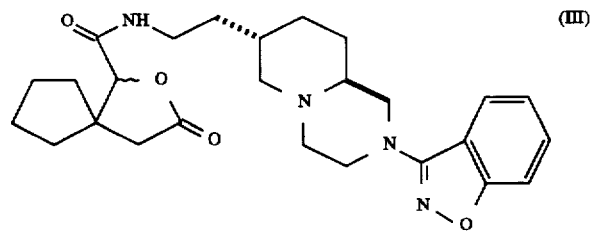

(III)

The new synthesis provides Compound I in an overall yield of approximately 8% based on pyridine diester, representing an approximate 5 fold improvement over previous syntheses.

In one aspect this invention is directed toward substantially optically pure intermediates and anxiolytic compounds of the formula:

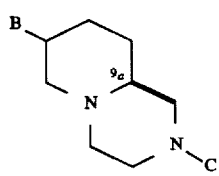

wherein the substituent B is either cis or trans to the $C_{9a}$–$C_1$ bond and is selected from the group consisting of

—$CH_2OH$,  —CHO,  —$CH_2OSO_2R$,  —$CH_2CN$,

—CH(OH)$CH_2NO_2$,  —CH=CH—$NO_2$,

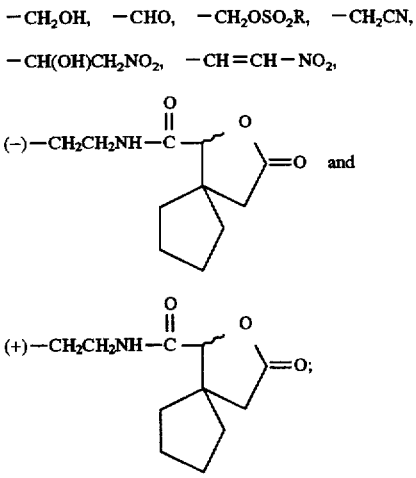

C is selected from the group consisting of —H,

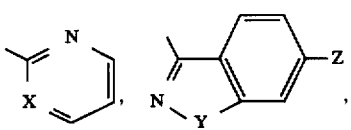

and a nitrogen protecting group which is removable by hydrogenation or acid treatment; and wherein R is ($C_1$–$C_8$) alkyl, phenyl or alkyl substituted phenyl; X is N or CH; Y is O or S; and Z is H or Cl; and with the proviso that when B is cis to the $C_{9a}$–$C_1$ bond, B must be —$CH_2OH$ or —CHO, and C must be a group other than —H; and acid salts thereof.

The preferred value of C is

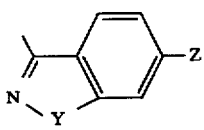

wherein Y is O and Z is H. The preferred value of R is methyl; and the preferred amine protecting group is tert-butoxycarbonyl.

In another aspect, this invention is directed toward a process for preparing a substantially optically pure compound of the formula

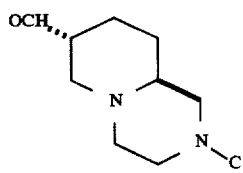

having (7R,9aS-Trans) configuration wherein C is selected from the group consisting of

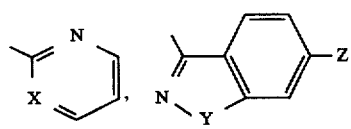

and a nitrogen protecting group which is removable by hydrogenation or acid treatment; wherein X is N or CH; Y is O or S and Z is H or Cl; comprising:

(a) reacting an activated form of C with a racemic compound of the formula

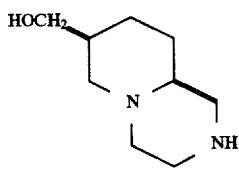

in a reaction inert solvent with an acid acceptor to form a racemic product which has formula

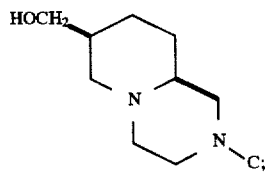

(b) reacting the racemic product of step (a) with a slight molar excess of D-(–)-tartaric acid in a reaction inert solvent forming two diasteromeric salts; (c) separating the diasteromeric salts of step (b) and treating the salt having (7S,9aS-Cis) configuration with base to obtain a compound which has the formula

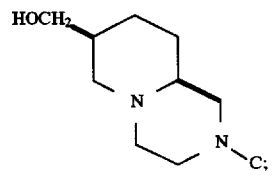

having (7S, 9aS-Cis) configuration; (d) reacting the product of step (c) with sulfur trioxide-pyridine complex and dimethylsulfoxide in a reaction inert solvent to form a product of the formula

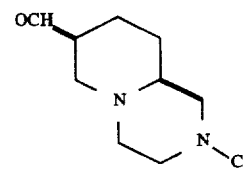

having (7S,9aS-Cis) configuration. Isomerizing the product of step id) with a sodium carbonate in a reaction (e) inert solvent to produce a compound of the formula

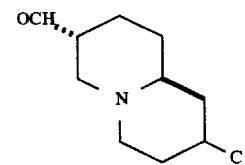

having (7R,9aS-Trans) configuration.

In a third aspect, this invention is directed toward a process for preparing a substantially optically pure compound of the formula

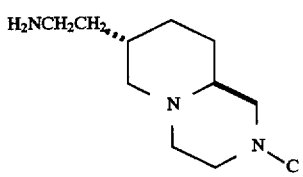

having (7S, 9aS-Trans) configuration wherein C is selected from the group consisting of H,

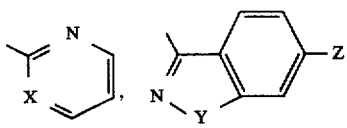

and a nitrogen protecting group which is removable by treatment with a strong acid; wherein X is N or CH; Y is O or S; and Z is H or Cl; comprising:

(a) reacting a compound of the formula

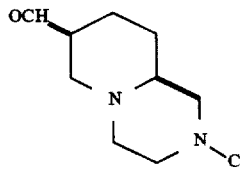

having (7S, 9aS-Cis) configuration wherein C is selected from the group consisting of

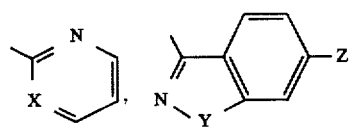

and a nitrogen protecting group removable by treatment with strong carbonate in a reaction inert solvent thereby converting said compound to the (7R, 9aS-Trans) configuration; and without isolation adding excess nitromethane and stirring until the reaction is complete to obtain a compound having the formula

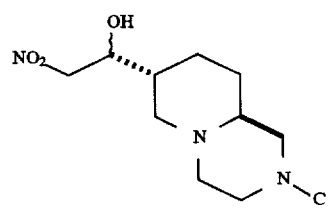

having (7R, 9aS-Trans) configuration;

(b) reacting the product of step (a) with an acid anhydride and a weak organic base in a reaction inert solvent to produce a compound having the formula

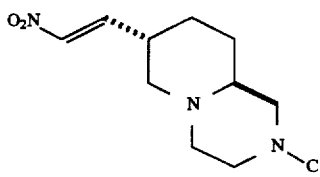

with a (7S, 9aS-Trans) configuration; (c) Reducing the compound of step (b) with hydrogen and a catalyst in a reaction inert solvent, or by complex hydride reduction (LiAlH$_4$) to produce a compound having the formula

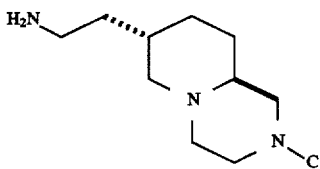

with a (7S, 9aS-Trans) configuration; wherein C is selected from the group consisting of

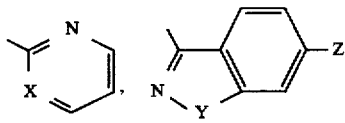

and a nitrogen protecting group which is removable by treatment with a strong acid, wherein X is NH or CH; Y is O or S; and Z is H or Cl;

(d) reacting the product of step (c) wherein C is an amine protecting group which is removable with strong acid, with strong acid in a reaction inert solvent and neutralizing with base producing a product having the formula

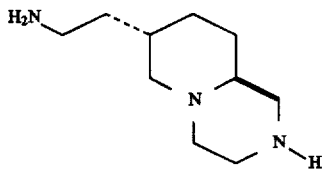

with a (7S,9aS-Trans) configuration.

In a fourth aspect, this invention is directed toward a process for preparing a substantially optically pure compound of the formula

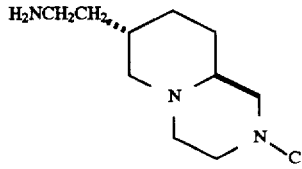

having (7S,9aS-Trans) configuration where in C is selected from the group consisting of H,

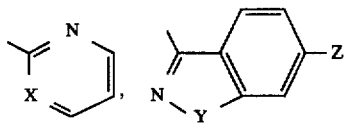

and a nitrogen protecting group which is removable by treatment with a strong acid; wherein X is N or CH; Y is O or S; and Z is H or Cl; comprising:

(a) reacting a compound of the formula

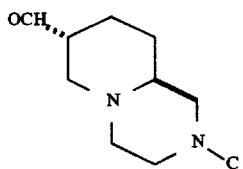

having (7R, 9aS-Trans) configuration wherein C is selected from the group consisting of

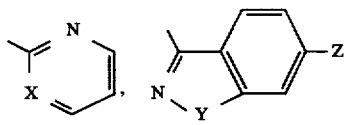

and a nitrogen protecting group removable by treatment with strong acid; wherein X is N or CH; Y is O or S and Z is H or Cl; with a reducing agent to produce a compound of the formula

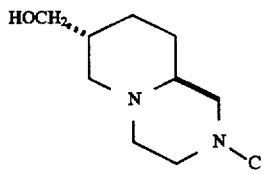

having (7R, 9aS-Trans) configuration;

(b) reacting the product of step (a) with methane sulfonyl chloride in a reaction inert solvent and in the presence of a base to form a compound of the formula

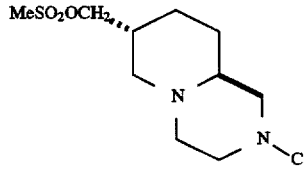

having (7R,9aS-Trans) configuration;

(c) reacting the product of step (b) with an alkali metal cyanide in a reaction inert solvent to form a compound of the formula

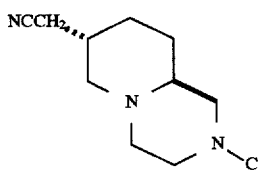

having (7S,9aS-Trans) configuration;

(d) reducing the product of step (c) to form a compound of the formula

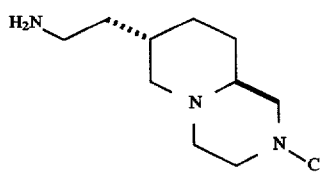

with a (7S,9aS-Trans) configuration; wherein C is selected from the group consisting of

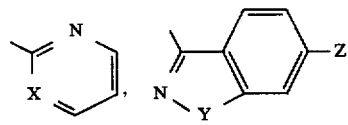

and a nitrogen protecting group which is removable by treatment with a strong acid, wherein X is NH or CH; Y is O or S; and Z is H or Cl;

(e) reacting the product of step (d) wherein C is an amine protecting group which is removable with strong acid, with strong acid in a reaction inert solvent and neutralizing with base to produce a compound having the formula

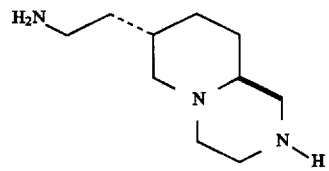

with a (7S,9aS-Trans) configuration.

DETAILED DESCRIPTION OF THE INVENTION

As used herein after, the expression "reaction inert solvent" refers to a solvent system in which the components do not interact with starting materials, reagents, intermediates or products in a manner which adversely affects the yield of the desired product.

The expression "nitrogen protecting group" as used hereinafter means a moiety which when coupled with a basic nitrogen will remain inert while other reactions are carried out. The nitrogen protecting group may then be removed under mild conditions yielding the free amino group. This invention contemplates two types of nitrogen protecting groups: those which may be removed by hydrogenation and those which may be removed by treatment with strong acid.

Examples of nitrogen protecting groups removed by strong acid are tert-butoxycarbonyl, meth- or ethoxycarbonyl, trimethylsilylethoxycarbonyl, 1-adamantoxycarbonyl, vinyloxycarbonyl, diphenyl methoxycarbonyl, trityl, acetyl and benzoyl. The group preferred is tert-butoxycarbonyl.

Examples of nitrogen protecting groups removed by hydrogen are benzyloxycarbonyl, 9-fluorenylmethyl oxycarbonyl, 2-phenylethyl oxycarbonyl, N-benzyl, p-methoxybenzyloxycarbonyl and p-nitrobenzyloxycarbonyl. The preferred group is benzyloxycarbonyl. As used hereinafter, the term "activated form of C" means a chemical derivative of

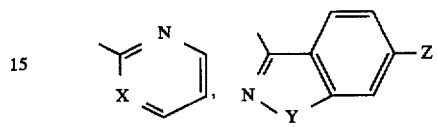

or a nitrogen protecting group which is capable of reacting with an NH group under relatively mild conditions. Examples of such activated forms include halo derivatives of the nitrogen heterocycles with chloro derivatives being preferred. The activated nitrogen protecting group may be in the form of the acid chloride or anhydride. When the nitrogen protecting group is tert-butoxycarbonyl the preferred activated form is di-tert-butyl dicarbonate.

The present invention is readily carried out using commercially available raw materials. Schemes 1 and 2 illustrate the present invention employing 1,2-benzisoxazolyl-3 as group C (defined herein above).

Prior to the present invention, Compound I and related anxiolytic agents were known but were obtainable only in low yields (See Scheme A) of about 1.5% from piperidine 2,5-dicarboxylate methyl ester. Especially difficult reaction steps were the conversion of the cis-piperidine-2,5-dicarboxylate ester to the corresponding trans ester (Compound A, Scheme A) which was achieved in only 30–40% yield, and the optical resolution step to produce Compound B (Scheme A) which yielded only 20% of the desired product.

I have found that the overall yield of the desired product may be improved about 5 fold (8% yield from pyridine diestar) by resolving the racemic hydroxymethyl intermediate (Compound IX, Scheme 1) to produce a 45% yield of the 7S, 9aS-Cis-7-hydroxmethyl compound (Compound X, Scheme 1). Conversion of Compound X proceeds to the desired 7R, 9aS-trans-7-hydroxy-methyl compound in 90% yield (See Compound XII, Scheme 1).

Scheme 1

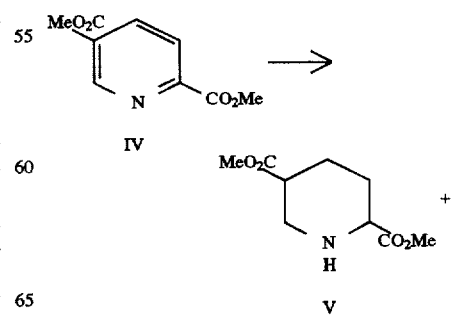

-continued
Scheme 1
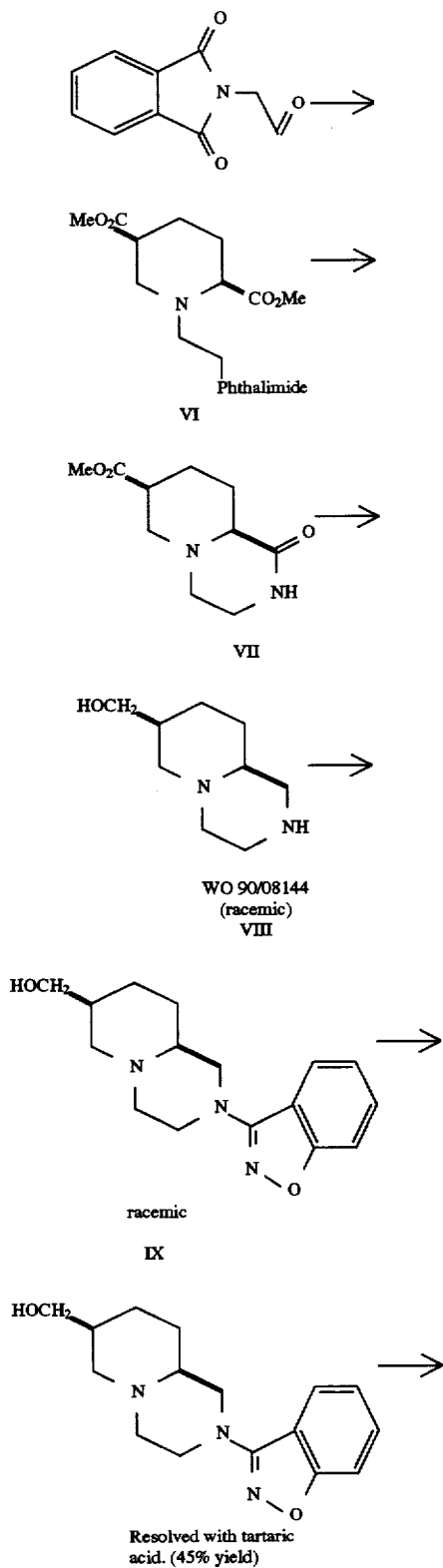
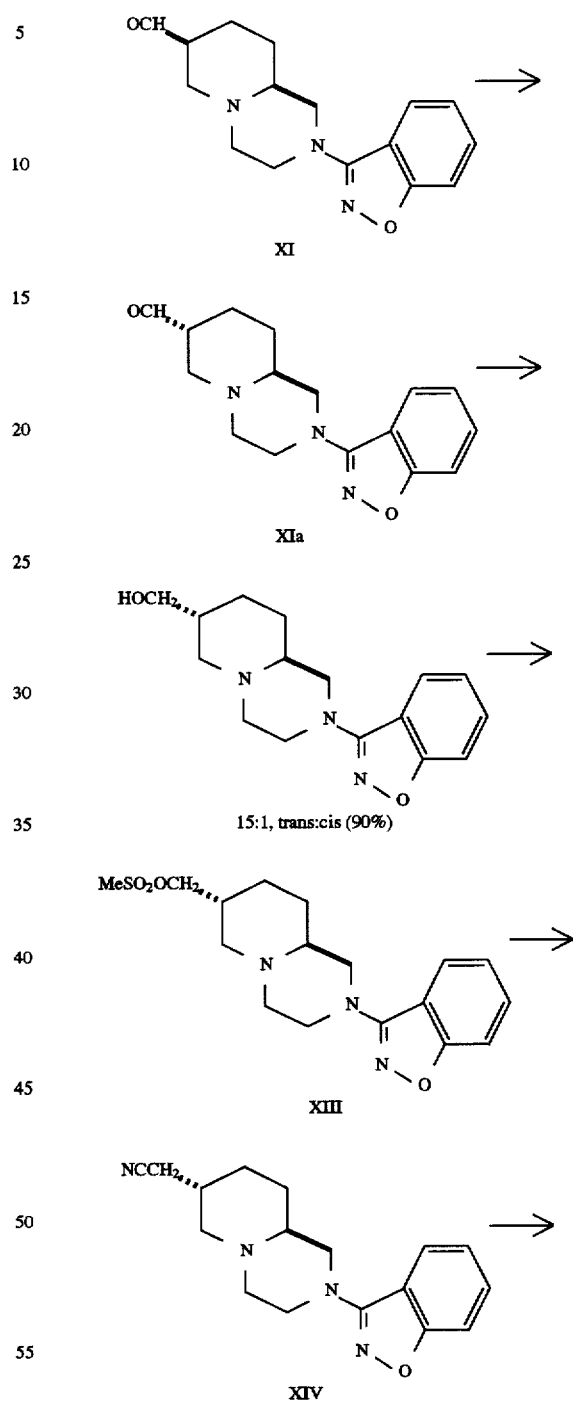

-continued
Scheme 1

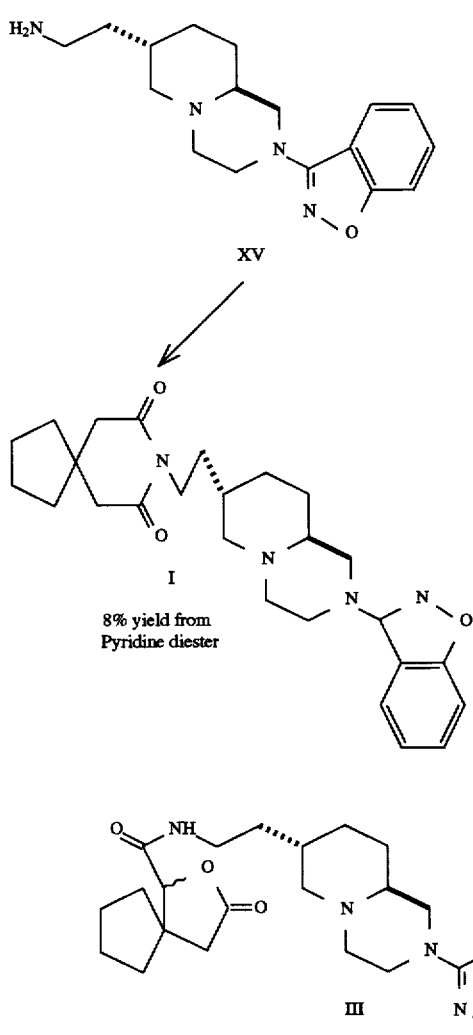

-continued
Scheme 2

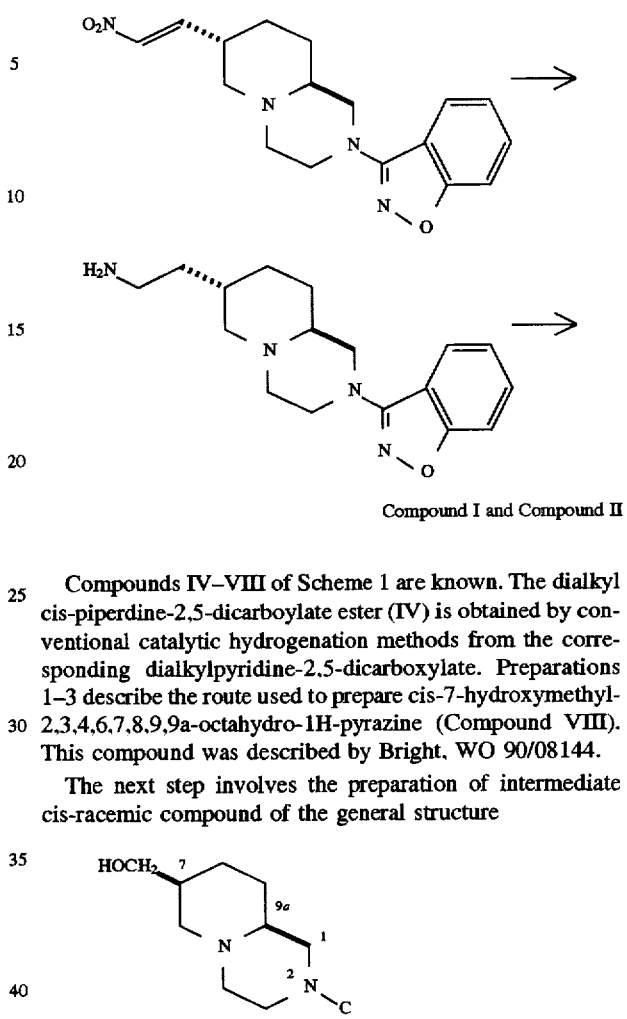

Compound I and Compound II

Compounds IV–VIII of Scheme 1 are known. The dialkyl cis-piperdine-2,5-dicarboylate ester (IV) is obtained by conventional catalytic hydrogenation methods from the corresponding dialkylpyridine-2,5-dicarboxylate. Preparations 1–3 describe the route used to prepare cis-7-hydroxymethyl-2,3,4,6,7,8,9,9a-octahydro-1H-pyrazine (Compound VIII). This compound was described by Bright, WO 90/08144.

The next step involves the preparation of intermediate cis-racemic compound of the general structure

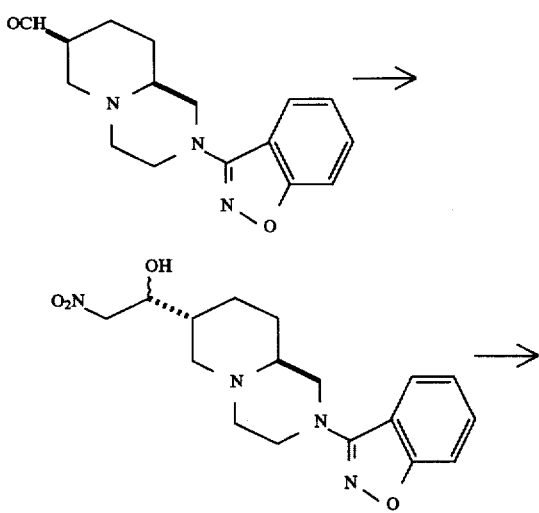

wherein C is as defined above.

This is accomplished by reacting Compound VIII with an activated form of C in a reaction inert solvent. If the activated form of C is a halo nitrogen heterocycle or an acid chloride, it is desirable to conduct the reaction at a moderately elevated temperature of about 50°–150° C. in the presence of an acid acceptor. A solvent such as pyridine may serve as the acid acceptor. If C is a nitrogen protecting group such as tert-butoxycarbonyl the activated form may be an anhydride. In this case the reaction may be conducted in a reaction inert solvent at room temperature.

Isolation and purification of the reaction product is accomplished by standard procedures which are obvious to a chemist of ordinary skill. One of ordinary skill in this art will also recognize that when C is an amine protecting group, it may be removed by any appropriate means such as acid treatment or reduction at any stage in the present process this converting C to H. This permits subsequent introduction of a heterocyclic C at the most convenient stage of synthesis.

The next step in the present process is preparation of the substantially optically pure compound of the structure with (7S, 9aS-Cis) configuration.

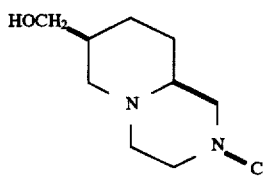

Wherein C is as above except that C may not be H.

Separation of optical isomers is accomplished by dissolving or suspending the racemic structure in a reaction inert solvent; methanol is preferred. A small molar excess of an optically active organic acid is added, D-(−) tartaric acid is preferred, and the mixture refluxed for 2–6 hours, cooled and the salt collected and purified. The free base may be obtained by standard methods such as by treatment with dilute sodium hydroxide in a two phase solvent system. This procedure is discussed in detail in Example 2 where C is 1,2-benzisoxazoyl-3yl and Example 11 where C is tert-butoxycarbonyl.

The next step in the present process is illustrated below:

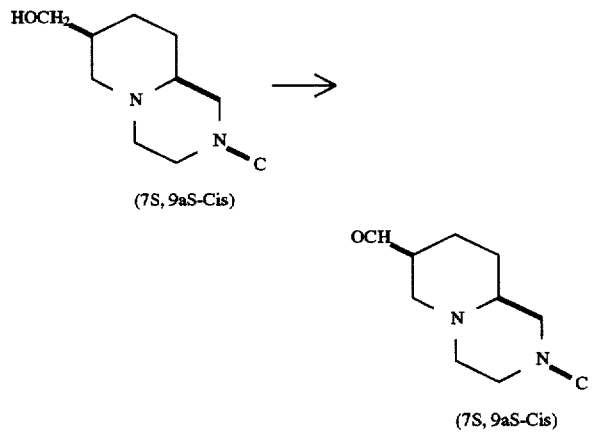

wherein C is as defined above except that C may not be H.

The conversion of hydroxymethyl to aldehyde is accomplished by oxidation with any suitable oxidizing agent. The preferred agent is sulfur trioxide pyridine complex and dimethylsulfoxide. It is preferred to conduct this reaction in a reaction inert solvent at a temperature of 0° C. to room temperature. Examples 3 and 12 illustrate this reaction.

The next step in the present process is as follows:

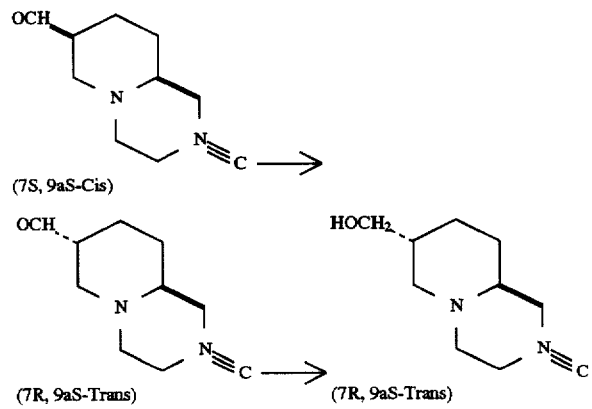

This reaction is conducted by isomerizing the cis-aldehyde to the trans-aldehyde with a base in a reaction inert solvent.

Sodium carbonate in methanol is preferred. The reaction is run at room temperature for 12–24 hours or until conversion to the trans-aldehyde is complete. The product may be isolated at this point but is more conveniently converted to the trans-hydroxymethyl compound by reduction of the aldehyde. The preferred reducing agent is sodium borohydride at approximately 0°–20° C. The product is isolated by standard means. This procedure is illustrated in Examples 4, 5 and 13.

The 7R, 9aS-trans-hydroxymethyl compound is converted by conventional chemical reactions to the corresponding 7S, 9aS-trans-2 ethylamino intermediate which in turn is converted to anxiolytic compounds of the type

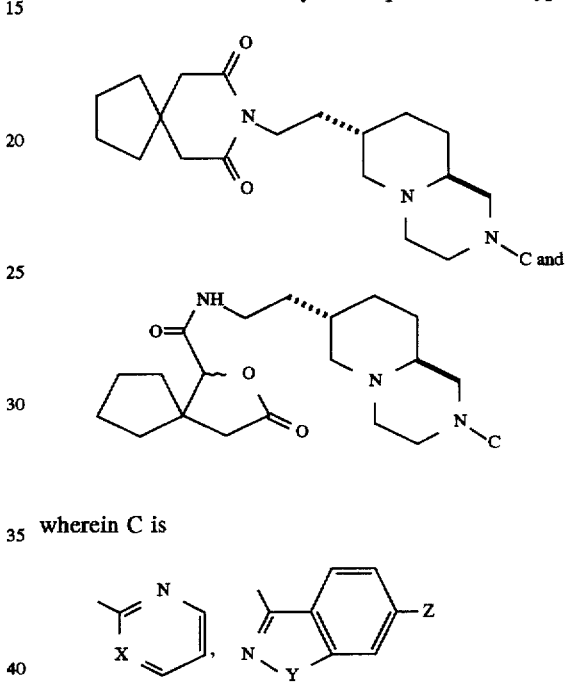

wherein C is and X is N or CH; Y is O or S and Z is H or Cl. These reactions are illustrated in Examples 6, 7, 18 and 19 and Preparations 4, 5 and 6.

In an alternative synthesis the 7S, 9aS-cis aldehyde is converted to the 7S, 9aS-trans-2-aminoethyl derivative by the following sequences of reactions

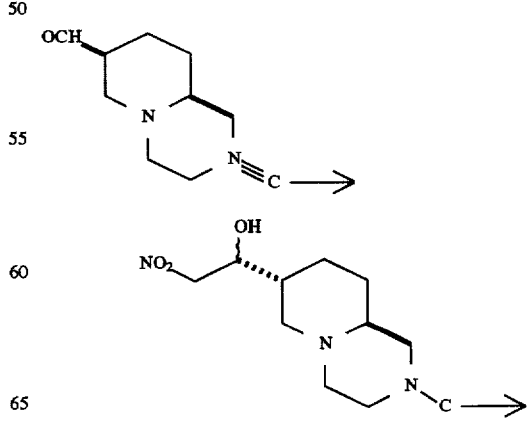

-continued

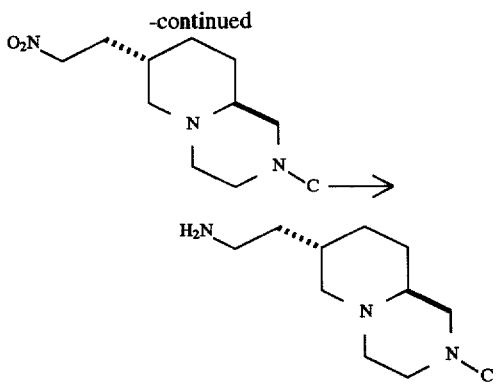

wherein C is selected from this group consisting of H

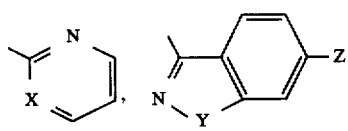

and a nitrogen protecting group which is removable by treatment with a strong acid; wherein X is N or CH; Y is O or S; and Z is H or Cl.

The first step in this sequence involves isomerization of the aldehyde. Sodium carbonate in a polar solvent such as methanol is preferred. The reaction is conducted at room temperature followed without isolation by addition of nitromethane to produce the trans-nitro alcohol.

The trans-nitroalcohol is dehydrated by treatment with an acid anhydride and weak organic base in a reaction inert solvent at room temperature. Acetic anhydride, dimethylaminopyridine and tetrahydrofuran are preferred.

The trans-nitro olefin is reduced by catalytic or metal hydride reduction in a reaction inert solvent to yield the 7S, 9aS-trans-2-aminoethyl derivative. Reduction by lithium aluminum hydride in tetrahydrofuran is the preferred procedure. This sequence of reactions is illustrated in Examples 8, 9, 14, 15 and Preparation 6.

Intermediate compounds useful for preparing other intermediate compounds and anxiolytic agents of the type

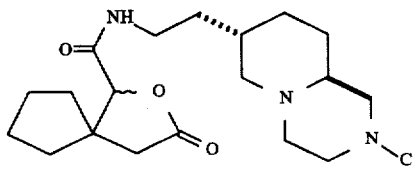

are prepared by halogenation of 3,3-tetramethyl glutaric anhydride at approximately 80°–120° C. neat or in a reaction inert solvent. Bromination without solvent is preferred. Hydrolysis of the halogen group in aqueous base at 100° followed by acidification yields 3-oxo-2-oxaspiro[4,4]-nonane-1-carboxylic acid.

The racemic acid is resolved by fractional crystallization of an optically active organic salt of the acid from a reaction inert solvent. d-(+)-Ephedrine and l-(−)-ephedrine are the preferred optically active organic bases and ethyl acetate is the preferred solvent.

The optically active acids are converted to the amides by reacting an activated form of the acid, preferably the acid chloride or the acid and a dehydrating agent with the trans-2-aminoethyl intermediate. The preferred method is to dehydrate a mixture of acid and amine in methylene chloride with n-propanephosphoric acid cyclic anhydride.

All clinically effective antipsychotic agents block dopamine binding to D-2 receptors, and demonstrate functional antagonism of dopamine-mediated behaviors in animals. Although the standard antipsychotics interact with a wide variety of neurotransmitter receptors, their potency in blocking D-2 binding is the only activity which shows a highly significant correlation with their oral clinical dosage (Creese et al., Science, 192:481–483, 1976). This clinical effect is believed to result from actions on mesolimbic-mesocortical dopamine projections to the forebrain, specifically inhibition of dopamine hypersensitivity caused by increased receptor density, as demonstrated in postmortem studies of schizophrenic brains (Lee et al., Nature, 274:897, 1978).

The relative ability of the present compounds of the formula III to displace binding at the D-2 receptors was determined according to standard radioligand homogenate binding techniques, as follows. Adult, male Sprague-Dawley rats (3 per assay) were decapitated, the brains quickly removed and caudate-putamen was dissected out. Tissue was homogenized in 50 volumes of ice-cold 50 mM Tris-HCl buffer containing 100 mM NaCl and 2 mM $MgCl_2$ and adjusted to pH 7.2. This mixture was centrifuged twice at 20,000×g for 15 minutes each, the supernatant being discarded each time and the pellet resuspended in fresh buffer with homogenization. The final pellet was resuspended in buffer to a concentration of 5.6 mg/ml. This tissue suspension was then added to tubes containing a fixed concentration of $^3$H-spiroperidol (0.2 nM), and various concentrations of test drug. Other tubes contained only buffer ("total") or a saturating concentration of (+)butaclamol (10 μM="blank"). The tubes (final volume—1.0 ml) were incubated at 37° C. for 15 minutes, then rapidly filtered under vacuum through glass fiber filters and rinsed with 12 ml of ice-cold buffer in a Brandel Cell Harvester. The filters were then removed and counted in a scintillation counter using 5 ml of Beckman ReadySafe scintillation fluid. The resulting counts were then used to generate the $IC_{50}$, or extrapolated concentration of test drug necessary to inhibit one-half of the binding, for each compound in question. (Method of Leysen et al., Biochemical Pharmacology, 27:307–316 (1978).

The antipsychotic activity of the compounds (III) is also demonstrated by their neuroleptic activity using methods based on standard procedures. In one method, adult male Sprague-Dawley rats are pretreated with appropriate doses of the test compound by subcutaneous injection. One half hour later, all rats are injected intraperitoneally with 1 mg/kg apomorphine hydrochloride dissolved in an 0.1% ascorbate solution. The rats are rated behaviorally according to the following stereotypy scale at 5, 15, 25, 35 and 45 minutes after the apomorphine injection: 0=alert but not moving, 1=moving about the cage, 2=discontinuous sniffing behavior, 3=continuous sniffing with discontinuous oral movements, and 4=continuous licking and chewing movements. Compounds with neuroleptic activity will lower the overall stereotypy score of the drug-treated groups, relative to untreated control rats, in proportion to their antagonist potency at the dopamine receptor.

The biological activity of the compounds of this invention makes them useful for treating psychotic disorders in human subjects. For example, these compounds are useful for treating psychotic disorders of the schizophrenic types, and in particular the compounds are useful for removing or ameliorating such symptoms as anxiety, agitation, excessive aggression, tension and social or emotional withdrawal in psychotic patients.

A compound of formula (III), or a pharmaceutically-acceptable salt thereof, is administered to a human subject either alone, or, preferably, in combination with pharmaceutically-acceptable carriers or diluents, in a pharmaceutical composition, according to standard pharmaceutical practice. These compositions are administered orally or parenterally. Parenteral administration includes especially intravenous and intramuscular administration. Additionally, in a pharmaceutical composition comprising a compound of formula (I), or a pharmaceutically-acceptable salt thereof, the weight ratio of active ingredient to carrier will normally be in the range from 1:6 to 2:1, and preferably 1:4 to 1:1. However, in any given case, the ratio chosen will depend on such factors as the solubility of the active component, the dosage contemplated and the precise route of administration.

For oral use of a neuroleptic agent of this invention, the compounds are administered, for example, in the form of tablets or capsules, or as an aqueous solution or suspension. In the case of tablets for oral use, carriers which can be used include lactose and corn starch, and lubricating agents, such as magnesium stearate, can be added. For oral administration in capsule form, useful diluents are lactose and dried corn starch. When aqueous suspensions are required for oral use, the active ingredient can be combined with emulsifying and suspending agents. If desired, certain sweetening and/or flavoring agents can be added. For intramuscular and intravenous use, sterile solutions of the active ingredient can be prepared, and the pH of the solutions should be suitably adjusted and buffered. For intravenous use, the total concentration of solutes should be controlled to render the preparation isotonic.

When an agent of this invention is to be used in a human subject to treat a psychotic disorder, the daily dosage will normally be determined by the prescribing physician. Moreover, the dosage will vary according to the age, weight and response of the individual patient as well as the severity of the patient's symptoms. However, in most instances, an effective amount for treating a psychotic disorder will be a daily dosage in the range from about 1 to 500 mg, preferably about 5 to 100 mg, in single or divided doses, orally or parenterally. In some instances it may be necessary to use dosages outside these limits.

The following examples are provided solely for the purpose of further illustration and are not intended to limit the invention which is defined by the claims.

EXAMPLE 1

Cis-7-hydroxymethyl-2-(1,2)(benzisoxazol-3-yl)-2,3,4,6,7,8,9,9a-octahydro-1H-pyrido[1,2-a]pyrazine

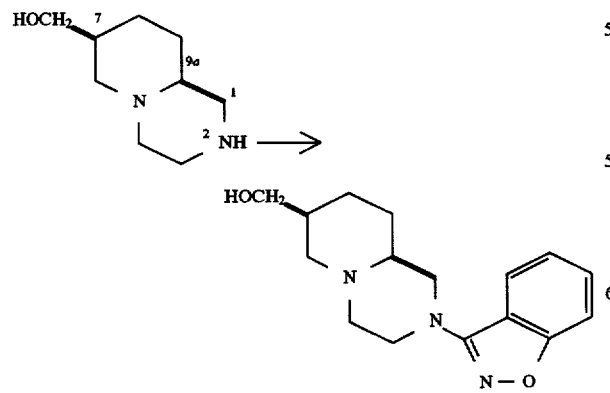

A solution of cis-7-hydroxymethyl-2,3,4,6,7,8,9,9a-octahydro-2H-pyrido[1,2-a]pyrazine (50 g, 0.29 mol),3-chloro-1,2-benzisoxazole (61.3 g, 0.39 mol) and 1,8-diazabicyclo[5.4.0]undec-7-ene (50 ml, 0.33 mol) in pyridine (100 ml) was heated at 115° C. under a nitrogen atmosphere for 18 h. The reaction was cooled to 45° C. and diluted with water to 800 ml volume. The crude solid was collected, air-dried, and then slurried in refluxing methanol (400 ml) for 1 h. After cooling to room temperature, the product was collected by filtration and washed with methanol to yield 75.4 g (91%). mp 180°–4.5° C.

EXAMPLE 2

(7S,9aS)-Cis-7-hydroxymethyl-2-(1,2-benzisoxazol-3-yl)-2,3,4,6,7,8,9,9a-octahydro-1H-pyrido[1,2-a]pyrazine

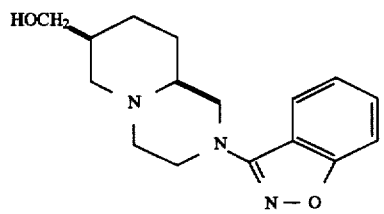

The racemic cis-alcohol (70.4 g, 0.245 mol) from Example 1 was slurried in methanol (1.2 L) at 60°–5° C. and D-(−)-tartaric acid (38.7 g, 0.258 mol) was added in one portion. Almost complete solution was achieved before the salt began to precipitate. The mixture was refluxed for 3 hours, and then cooled to room temperature and filtered. The isolated solid was slurried in methanol (50 ml) and water (150 ml) at 60° C. to give a thin slurry which was diluted with methanol (1 L) and refluxed for 18 hours. After cooling the mixture, the salt was collected by filtration and dried in vacuo. The yield was 48.95 g, 45.7% mp 207°–9° C.; $[\alpha]_D$–37.61° (c=0.521, water). Anal. Calcd. for $C_{20}H_{27}N_3O_8$: C, 54.91; H, 6.22; N, 9.61. Found: C, 54.79; H, 6.37; N, 9.45.

The salt (48.7 g, 0.11 mol) was added to a stirred mixture of methylene chloride (500 ml) and 2N NaOH (110 ml). The pH of the aqueous layer was 12. The organic layer was separated and the aqueous extracted with methylene chloride a second time. The combined organics were washed with brine and dried over $MgSO_4$. Filtration of the drying agent and evaporation yielded the optically active cis-diamine, 29.45 g; 93.3%. mp 127°–30° C., $[\alpha]_D$–45.52° (c=0.692, MeOH). Anal. Calcd. for $C_{16}H_{21}N_3O_2C$, 66.88; H, 7.37; N, 14.62. Found: C, 66.72; H, 7.25; N, 14.52.

EXAMPLE 3

(7S,9aS)-Cis-7-formyl-2-(1,2-benzisoxazol-3-yl)-2,3,4,6,7,8,9,9a-octahydro-1H-pyrido[a]pyrazine

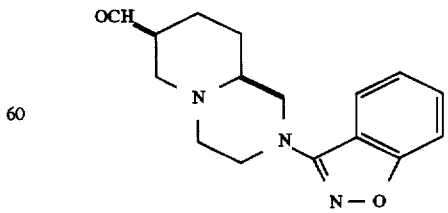

The optically active cis-alcohol (6 g, 21 mmol) from Example 2 was dissolved in methylene chloride (160 ml)

and dimethylsulfoxide (1.5 ml) with diisopropylethylamine (14.5 ml, 84 mmol) and cooled to 0° C. in an ice water bath. A solution of sulfur trioxide pyridine complex (10 g, 63 mmol) in dimethylsulfoxide (15 ml) was added dropwise under N₂. The reaction was allowed to warm to room temperature and stirred overnight. Water (75 ml) was added and the reaction stirred for 10 minutes. The layers were separated and the organics were washed with water, with brine, and were dried over MgSO₄. The solvent was removed in vacuo to give the product as a crude oil which solidified. Ethyl acetate (75 ml) was added followed by a solution of sodium bisulfite (4 g) in water (50 ml) and the mixture was stirred for 20 minutes. The layers were separated and the aqueous was extracted with ethyl acetate. The resulting aqueous layer was combined with fresh ethyl acetate and sodium carbonate (5 g) and stirred for 15 minutes. The layers were separated and the organics were dried over MgSO₄. The solution was filtered and evaporated in vacuo to provide the purified aldehyde as a white solid, 4.68 g, 79% yield. NMR (CDCl₃, 300 MHz) δ 9.8 (s, 1, CHO), 7.67 (dd, 1), 7.45 (m, 2), 7.20 (m, 1), 3.95 (m, 1), 3.80 (m, 1), 3.28 (m, 2), 2.5–2.15 (m, 5), 1.5 (m, 2), 1.3 (m, 1).

EXAMPLE 4

(7R,9aS)-Trans-7-formyl-2-(1,2-benzisoxazol-3-yl)-2,3,4,6,7,8,9,a-octahydro-1H-pyrido[1,2-a]pyrazine

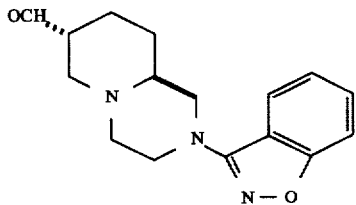

The optically active cis-aldehyde from Example 3 (0.4 g) was dissolved in methanol (10 ml) with sodium carbonate (30 mg) and stirred at room temperature for 18 hours. The reaction was followed by tlc on silica gel plates with 1:1 ethyl acetate: chloroform as the solvent. The cis-aldehyde has an Rf of 0.44 while the trans-aldehyde has an Rf of 0.12. The equilibrium point of the mixture is ca. 15:1, trans: cis. The reaction mixture was evaporated and ethyl acetate and water were added. The organic layer was washed with brine, dried over MgSO₄, and evaporated to give the trans-aldehyde with 10% of the cis-aldehyde. NMR (CDCl₃, 300 MHz) δ 9.63 (s, 1, CHO trans).

EXAMPLE 5

(7R,9aS)-Trans-7-hydroxymethyl-2-(1,2-benzisoxazol-3-yl)-2,3,4,6,7,8,9,9a-octahydro-1H-pyrido[1,2-a]pyrazine

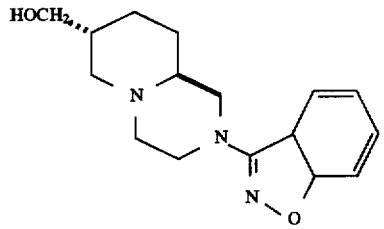

A solution of the cis-aldehyde from Example 3 (4.65 g, 0.016 mol) in methanol (75 ml) was stirred at room temperature with sodium carbonate (0.152 g, 0.0014 mol) for 18 hours. During this time, tlc showed the conversion to trans-aldehyde, The reaction was cooled to 5° C. and a solution of sodium borohydride (0.31 g, 8.2 mmol) in methanol (5 ml) was added dropwise. The methanol was removed by evaporation in vacuo and the crude product was dissolved in ethyl acetate and water. The ethyl acetate layer was washed with water and brine, dried over MgSO₄. and evaporated. The crude material was crystallized from isopropanol (30 ml) and hexanes (10 ml). The mother liquor was evaporated and the residue chromatographed over silica gel with acetone to provide additional pure trans-alcohol. The first crop material and the chromatographed sample were combined and recrystallized from isopropyl alcohol (25 ml) and hexanes (25 ml) to give 3.36 g (72%) of analytically pure trans-alcohol. mp 158°–9° C., [α]$_D$ –9.06° (C=0.552, MeOH) Anal. Calcd. for C₁₆H₂₁N₃O₂: C, 66.88; H, 14.62. Found: C, 67.10; H, 7.60; N, 14.71.

EXAMPLE 6

(7R,9aS)-Trans-7-(methanesulfonyloxymethyl)-2-(1,2-benzisoxazol-3-1)-2,3,4,6,7,8,9,9a-octahydro-1-H-pyrido[1,2-a]pyrazine

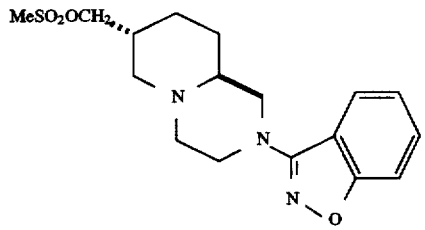

The trans-alcohol from Example 5 (3.62 g, 12.6 mmol) was suspended in methylene chloride (60 ml) with triethylamine (1.95 ml, 14 mmol) and stirred at 0° C. under nitrogen while a solution of methanesulfonyl chloride (1.1 ml, 14 mmol) in methylene chloride (10 ml) was added dropwise. The reaction was allowed to warm to room temperature and after 2 hours, a tlc on silica gel with 9:1, methylene chloride:methanol showed the reaction was complete. The reaction mixture was washed with aqueous sodium carbonate and dried over MgSO₄. The drying agent was removed by filtration and the solvent was evaporated in vacuo to provide the title product as a white solid (4.4 g, 96.5%) with traces of triethylamine. NMR (CDCl₃, 300 MHz) δ 7.66 (d, 1), 7.44 (m, 2), 7.19 (dt, 1), 4.0 (m, 3), 3.73 (m, 1), 3.25 (tit, 1), 3.0 (s over m, 1), 2.83 (m, 2), 2.48 (dt, 1), 2.14 (m, 2), 71.9 (dt, 1), 1.83 (m, 1), 1.72 (m, 1), 1.34 (m, 1).

EXAMPLE 7

7S,9aS)-Trans-7-(cyanomethyl)-2-(1,2-benzisoxazol-3-yl)-2,3,4,6,7,8,9,9a-octahydro-1H-pyrido[1,2-a]pyrazine

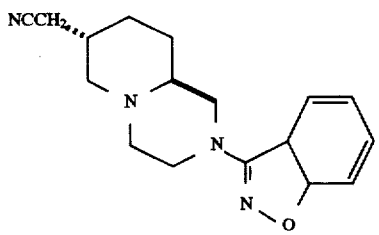

The trans-mesylate from Example 6 (4.4 g, 12 mmol) and sodium cyanide (1.2 g, 24 mmol) were heated in dimethylformamide (25 ml) at 100° C. under nitrogen for six hours. The reaction was cooled to room temperature and diluted to 150 ml volume with water and the mixture granulated for 45 minutes. The solid was collected by filtration, dissolved in methylene chloride and washed with aqueous sodium carbonate solution and brine. The organic solution was dried over MgSO₄, filtered, and evaporated in vacuo to afford the title compound as a white solid, 3.32 g, 93.5%. mp 184°–86° C.; NMR (CDCl₃, 300 MHz) δ 7.68 (d, 1), 7.46 (m, 2), 7.20 (dt, 1), 3.98 (dq, 1), 3.87 (dt, 1), 3.28 (dt, 1), 2.96 (m, 1), 2.86 (m, 2), 2.50 (dt, 1), 2.30 (d, 2), 2.21–1.68 (m, 5), 1.38 (dq, 1), 1.19 (dq, 1).

EXAMPLE 8

(7R,9aS)-Trans-7-(1-hydroxy-2-nitroethyl)-2-(1,2-benzisoxazol-3-yl)-2,3,4,6,7,8,9,9a-octahydro-1H-pyrido[1,2a]pyrazine

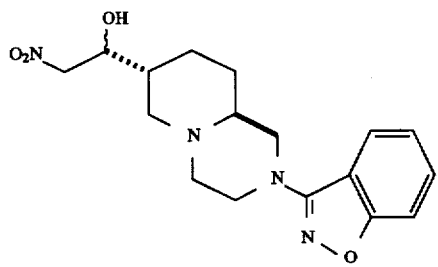

The optically active cis-aldehyde from Example 3 (3.5 g, 12.3 mmol) was equilibrated to the trans-aldehyde in methanol (50 ml) with sodium carbonate (0.125 g, 1.2 mmol) over 4 hours at room temperature. Nitromethane (3 g, 49 mmol) was added to the mixture and after 1 hour precipitation of the nitroalcohol began. The title compound was collected over three crops as a white solid, 3.65 g (82%). mp 153°–6° C.; NMR (DMSO-d₆, 300 MHz) δ 8.0 (d, 1), 7.57 (d, 2), 7.29 (m, 1), 5.45 (d, 1), 4.79 (dd, 1), 4.30 (dd, 1), 3.89 (m, 3).

EXAMPLE 9

(7S,9aS)-Trans-7-(2-nitroethylenyl)-2-(1,2-benzisoxazol-3-yl)-2,3,4,6,7,8,9,9a-octahydro-1H-pyrido[1,2-a]pyrazine

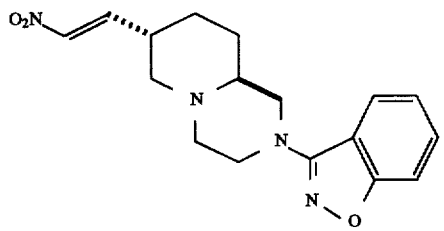

The optically active nitroalcohol from Example 8 (1.9 g, 5.22 mmol) was treated with acetic anhydride (1 ml) and dimethylaminopyridine (30 mg, 0.25 mmol) in tetrahydrofuran (20 ml) at room temperature. After 2.5 hours at room temperature, this was added to sodium carbonate (1.5 g, 14 mmol) in methanol (30 ml) and stirred for 2 hours. The reaction was concentrated in vacuo to 10 ml and partitioned between ethyl acetate and water. The organic layer was washed with water, dried over MgSO₄ and evaporated in vacuo to afford the title product as a yellow solid; 1.42 g, 83% yield. Rf 0.65 (silica gel, 9:1-methylene chloride: methanol) NMR (CDCl₃, 300 MHz) δ 7.68 (dd, 1), 7.45 (m, 2), 7.18 (m, 2), 6.96 (d, 1), 4.00 (m, 1), 3.88 (m, 1), 3), 2.65 (m, 1), 2.52 (dt, 1), 2.21 (m, 1), 2.04 (m, 1), 1.93 (m, 1), 1.76 (m, 1), 1.36 (m, 2).

EXAMPLE 10

Racemic cis-7-hydroxymethyl-2-(tert.-butoxycarbonyl)-2,3,4,6,7,8,9,9a-octahydro-1H-pyrido[1,2-a]pyrazine

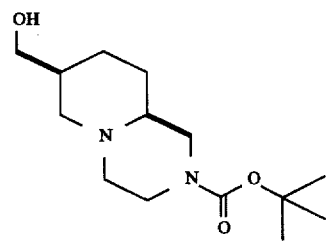

A suspension of cis-7-hydroxymethyl-2,3,4,6,7,8,9,9a-octahydro-2H-pyrido[1,2-a]pyrazine (4.4 g, 25.6 mmol) in methylene chloride (50 ml) was stirred at room temperature while a solution of di-tert.-butyl dicarbonate (5.7 g, 26.1 mmol) in methylene chloride (50 ml) was added dropwise. The solution was stirred at room temperature overnight. The reaction was washed with water, with brine and was dried over MgSO₄. Evaporation in vacuo afforded the title product as a colorless oil which slowly crystallized. 6.42 g, 93%.

EXAMPLE 11

(7S9aS)-Cis-7-hydroxymethyl-2-(tert-butoxycarbonyl)-2,3,4,6,7,8,9,9-a-octahydro-1H-pyrido[1,2-a]pyrazine

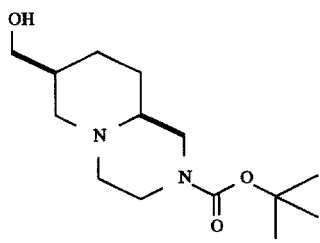

The racemic diamino-alcohol from Example 10 (38 g, 0.141 mol) in methanol (340 ml) at room temperature was treated with (−)-tartaric acid (21 g, 0.141 mol) in one portion. After a short time the solution became cloudy and precipitation began. The mixture was stirred overnight. The solid was collected by filtration and was washed with methanol. This initial salt was stirred with fresh methanol (200 ml) overnight. The solid was filtered and dried in vacuo to provide the pure tartrate salt; 23.75 g, 40% yield. mp 195°–6° C.; $[\alpha]_D$–36.86°(c=0.765, water) Anal. Calcd. for $C_{18}H_{32}N_2O_9$:C, 51.42; H, 7.67; N, 6.66. Found: C, 51.74; H, 7.54; N, 6.52.

The tartrate salt was partitioned between methylene chloride and 1N NaOH (pH 10.5). The layers were separated and the aqueous layer extracted a second time with methylene chloride. The combined organic layers were dried over MgSO$_4$ and concentrated in vacuo to provide the title compound as an oil which slowly crystallized. mp; 60°–5° C.; $[\alpha]_D$–35.03° C. (c=0.942, MeOH). $^{13}$CMR (CDCl$_3$, 300 MHz) δ 154.463, 79.677, 67.341, 60.776, 60.249, 58.119, 54.813, 48.747, 43.901, 34.349, 28.382, 26.794, 26.076.

EXAMPLE 12

(7S,9aS)-Cis-7-formyl-2-(tert.-butoxylcarbonyl)-2,3,4,6,7,8,9,9a-octahydro-1H-pyrido[1,2-a]pyrazine

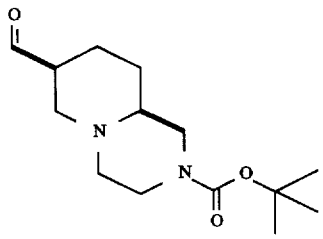

The optically active cis-alcohol (6.13 g, 22.7 mmol) from Example 11 was oxidized with sulfur trioxide pyridine complex (8.8 g, 55.5 mmol), diisopropylethylamine (15.5 ml, 89 mmol) and dimethylsulfoxide (23 ml) in methylene chloride (150 ml) as described in Example 3 and purified through the bisulfite procedure to provide the title material, 3.1 g, 50% yield, as a yellow oil. Rf 0.48 (70% chloroform: 30% ethyl acetate). NMR (CDCl$_3$, 300 MHz) δ 9.68 (s, 1, CHO), 1.37 (s, 9, Me$_3$C).

EXAMPLE 13

(7R,9aS)-Trans-7-formyl-2-(tert-butoxylcarbonyl)-2,3,4,6,7,8,9,9a-octahydro-1H-pyrido[1,2-a]pyrazine and (7R,9aS)-trans-7-hydroxymethyl)-2-(tert-butoxycarbonyl)-2,3,4,6,7,8,9,9a-octahydro-1H-pyrido[1,2-a]pyrazine

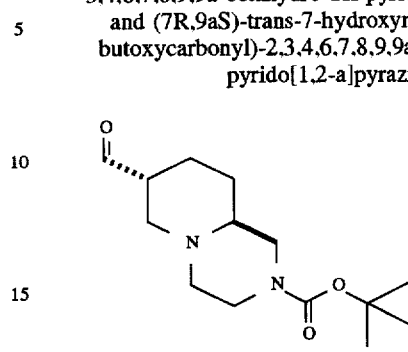

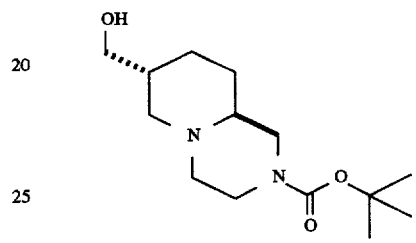

The optically active cis-aldehyde (0.28 g, 1 mmol) in methanol (10 ml) was stirred with sodium carbonate (80 mg, 0.75 mmol) at room temperature for 18 hours. The tlc of the mixture at this point showed that the conversion to the more polar trans-aldehyde was complete. (tlc: silica gel; 70% CHCl$_3$: 30% ethyl acetate) Sodium borohydride (10 mg) was added to the solution. After 0.5 hour, the reaction was concentrated and ethyl acetate and water were added. The desired optically active trans-alcohol was recovered from the organic layer and purified by flash chromatography over silica gel with acetone; 0.15 g, 54% yield. $[\alpha]_D$–2.21° (c=0.317, CHCl$_3$)

EXAMPLE 14

(7R,9aS)-Trans-7-(1-hydroxy-2-nitroethyl)-2-(tert.-butoxycarbonyl)-2,3,4,6,7,8,9,9a-octahydro-1H-pyrido[1,2-a]pyrazine

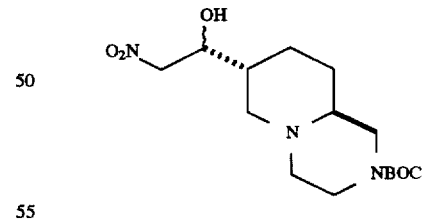

The optically active cis-aldehyde from Example 12 (3 g, 11.2 mmol) in methanol (30 ml) was stirred with sodium carbonate (300 mg, 2.8 mmol) at room temperature for 18 hours. Nitromethane (5 ml) was added to the reaction and the solution was stirred for 72 hours. The reaction was concentrated in vacuo and partitioned between ethyl acetate and water. The ethyl acetate layer was washed with water, with brine, and was dried over MgSO$_4$. Evaporation gave the crude product which was purified by flash chromatography over silica gel with ethyl acetate as eluant. The title product was a colorless oil which slowly crystallized, 1.78 g, 48%. mp 142°–50° C. $^{13}$CMR (CDCl$_3$, 300 MHz) δ 154.547, 79.886, 79.391, 71.109, 70.440, 60.519, 60.422, 57.508, 57.026, 54.737, 39.790, 39.708, 28.397, 26.555, 24.892.

EXAMPLE 15

(7S,9aS)-Trans-7-(2-nitroethylenyl)-2-(tert.-butoxycarbonyl)-2,3,4,6,7,8,9,9a-octahydro-1H-pyrido[1m2-a]pyrazine

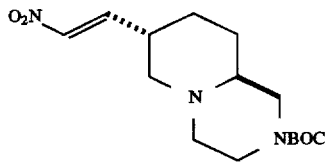

The optically active nitroalcohol from Example 14 (1.2 g, 3.65 mmol) and acetic anhydride (0.7 ml, 7.5 ml) in tetrahydrofuran (20 ml) were stirred at room temperature while dimethylaminopyridine (25 mg, 0.2 mmol) was added. After 0.5 hour, tic (silica gel, ethyl acetate) showed no alcohol remained and sodium carbonate (1 g, 9.4 mmol) was added and the reaction was stirred for 2 hours. The reaction was concentrated to half volume in vacuo and water and ethyl acetate were added. The nitroolefin was recovered from the organic layer as a yellow oil which slowly crystallized, 1 g, 90% yield. NMR (CDCl$_3$, 300 MHz) δ 7.10 (q, 1), 6.94 (d, 1), 1.46 (s, 9). $^{13}$CMR (CDCl$_3$) δ 154.368, 143.225, 139.359, 79.843, 60.010, 58.925, 54.496, 36.289, 28.965, 28.395.

EXAMPLE 16

3-Oxo-2-oxaspiro[4,4]-nonane-1-carboxylic acid

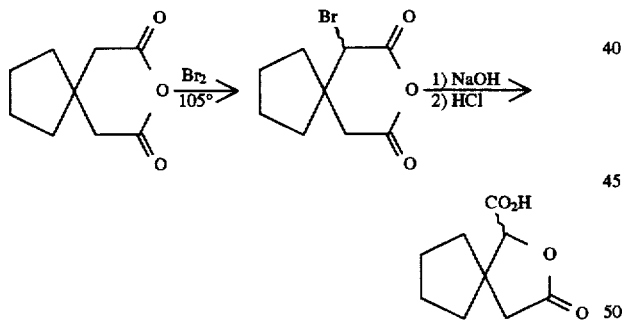

3,3-Tetramethylene glutaric anhydride (5 g, 30 mmol) was heated to 105° C. and irradiated with a sun lamp while bromine (2 ml, 38.7 mmol) was added dropwise. After the bromine color dispersed, the reaction was cooled to room temperature and 2.4M NaOH (50 ml) was added and the mixture was heated to reflux for 2 hours. The solution was cooled to room temperature and the pH was adjusted to pH 2 and stirred in a ice water bath for 0.5 hour. The precipitate (unreacted 3,3-tetrametylene glutaric acid) was filtered and discarded. The filtrate was extracted three times with ethyl acetate and the combined organics were washed with brine and dried over MgSO$_4$. Evaporation yielded the title acid as a colorless oil, 5 g, 90%. NMR (CDCl$_3$, 300 MHz) δ 7.95 (broad s, OH), 4.65 (s, 1, methine), 2.61 and 2.35 (ab, 2, methylene), 1.9–1.45 (m, 8, tertramethylene).

EXAMPLE 17

(−)-3-Oxo-2-oxaspiro[4,4]-nonane-1-carboxylic acid and (+)-3-oxo-2-oxaspiro[4,4]-nonane-1-carboxylic acid

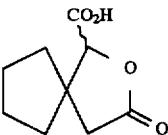

The racemic acid from Example 16 (6.65 g, 36.1 mmol) and d-(+)-ephedrine (6.03 g, 36.2 mmol) were heated in ethyl acetate (175 ml) to give a solution. The heat was removed and the solution was seeded with crystals obtained from a test tube reaction. Crystallization of the desired diastereomer proceeded from the warm solution at temperatures greater than 40° C.; precipitation at room temperature gave a racemic mixture. The precipitate was stirred at room temperature for 0.5 hour and collected by filtration. 2.65 g, 21% yield; mp 161°–3° C.; [α]$_D$–6.47° (c=0.51, MeOH). NMR (CDCl$_3$, 300 MHz) δ 7.25 (m, 5), 5.33 (s, 1), 4.63 (s, 1), 3.40 (m, 1), 2.80 (s, 3), 2.53 and 2.32 (ab, 2), 2.02–1.40 (m, 8), 1.09 (d, 3). Anal. Calcd. for C$_{19}$H$_{27}$NO$_5$: C, 65.31; N, 4.01. Found: C, 65.19; H, 7.78; N, 4.01.

The d-(+)-ephedrine salt of the levorotatory acid (1.6 g, 4.6 mmol) was dissolved in water and the pH lowered to pH 2 with 2N HCl. The acid was extracted three times with ethyl acetate. The combined organics were washed with brine, dried over MgSO$_4$ and evaporated in vacuo to provide the levorotatory acid as a colorless oil; 0.84 g, 100% yield. [α]$_D$–30.76° (c=0.998, CHCl$_3$). NMR (CDCl$_3$, 300 MHz) δ 8.68 (s, 1), 4.69 (s, 1, methine), 2.64 and 2.39 (ab, 2, methylene), 1.94–1.55 (m, 8).

The filtrates from the above resolution were combined and the racemic acid enriched in the dextrorotatory acid was recovered. This material (4.81 g, 26 mmol) and l-(−)-ephedrine (4.3 g, 26 mmol) in 126 ml hot ethyl acetate as above provided the (−)-ephedrine salt of the (+)-acid; 3.24 g, 36% yield. mp 160–3° C; [α]$_D$+4.96° (c=0.565, CHCl$_3$). Anal. Calcd. for C$_{18}$H$_{27}$NO$_5$: C, 65.31; H, 7.79; N, 4.01. Found: C, 65.39; H 7.64; N, 4.06.

The salt (1.65 g, 4.73 mmol) was treated as described for the enantiomer to afford the dextrorotatory acid in quantitative yield; [α]$_D$+29.63° (c=0.999, CHCl$_3$).

EXAMPLE 18

(−)-3-Oxo-N-[2-[7-(2-(3-(1,2-benzisoxazolyl)-2,3,4,6,(7S),8,9, (9aS)-octahydro-1H-pyrido[1,2-a]pyrazinyl)]-ethyl]2-oxaspiro-[4,4]-nonane-1-carboxamide

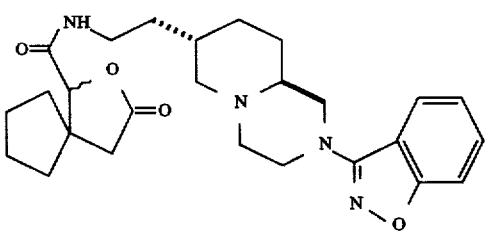

The (−)-acid from Example 17 (190 mg, 1.03 mmol) and the (−)-amine (316 mg, 1.05 mmol) from Preparation 4, were combined in methylene chloride (10 ml) with N-methylmorpholine (0.16 ml, 1.46 mmol). To the resulting suspension was added n-propanephosphoric acid cyclic anhydride (1.28 g, 2 mmol, 50% by weight in methylene chloride). After stirring at room temperature overnight, the reaction was washed with water, with brine and was dried over $MgSO_4$. The crude product was recovered by evaporation and purified by chromatography over silica gel with ethyl acetate as eluant. The yield was 0.25 g, 48%. mp 119°–28° C.; $[\alpha]_D$–14.76° (c=0.42, $CH_2Cl_2$). $^{13}$CMR ($CDCl_3$) δ 174.503, 167.348, 163.971, 161.061, 129.512, 122.270, 122.146, 116.128, 110.479, 83.586, 61.316, 60.087, 54.126, 53.692, 50.861, 48.225, 43.000, 36.528, 36.415, 34.254, 33.788, 32.600, 30.282, 29.250, 24.024, 23.429.

EXAMPLE 19

(+)-3-Oxo-N-[2-[7-(2-(3-(1,2-benzisoxazolyl)-2,3,4,6,(7S), 8,9, (9aS)-octahydro-1H-pyrido[1,2-a]pyrazinyl)]-ethyl]2-oxaspiro-[4,4]-nonane-1-carboxamide

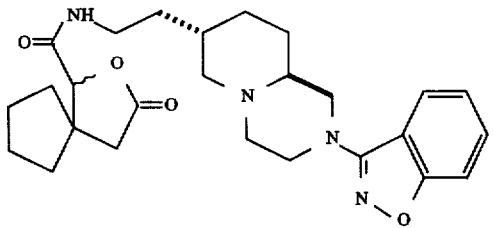

In the same manner as Example 18, the (+)-acid from Example 17 (0.3 g, 1.63 mmol) was reacted with the (–)-amine (0.4 g, 1.35 mmol) to provide the (+)-diastereomeric amide, 0.35 g, 55.5% yield. mp 84°–89° C.; $[\alpha]_D$+7.89° (c=0.494, $CH_2Cl_2$). NMR same as the (–)-diastereomer.

EXAMPLE 20

(7S,9aS)-Trans-7-(2-aminoethyl)-2-(1,2-benzisoxazol-3-yl)-2,3,4,6,7,8,9,9a-octahydro-1H-pyrido[1,2-a]pyrazine

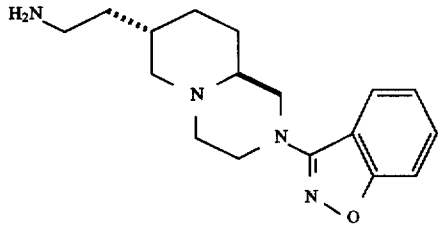

A. The trans-nitrile from Example 7 (3.3 g, 11 mmol) was added as a solid in portions to lithium aluminum hydride (0.7 g, 18 mmol) in tetrahydrofuran (60 ml) over three minutes. The reaction was heated to reflux for 24 hours, then cooled to room temperature. Water (0.7 ml in 10 ml tetrahydrofuran) was added slowly followed by 15% NaOH (0.7 ml) and water (2 ml). After stirring for 3 hours to decompose excess hydride, the mixture was filtered and the solids washed with hot tetrahydrofuran. The organic solvent was removed in vacuo and the residue was dissolved in methylene chloride and washed with aqueous sodium carbonate. The organic solution was dried over $MgSO_4$, filtered, and evaporated to afford the crude amine. This was dissolved in ethanol (48 ml). d-(+)-mandelic acid (1.6 g, 10.7 mmol) was added, and the mixture was heated to reflux briefly. The purified amine mandelate salt was isolated by filtration and was dried in vacuo; 2.15 g, 4.3% yield.

B. The nitroolefin from Example 9 (1.5 g, 4.6 mmol) was reduced to the title compound with 1M lithium aluminum hydride in tetrahydrofuran (14 ml, 14 mmol). The work up was the same as that described for the nitrile reduction and the, pure amine was isolated as the mandelate salt, 0.6 g, 37.5%.

PREPARATION 1

Dimethyl cis-N-(2-(phthalimido)ethyl)-piperdine-2,5-dicarboxylate

Method A

A solution of 12.0 g (45.6 mmol) phthalimido acetaldehyde diethyl acetal (Aldrich Chemical Co., Inc.) in 36 ml acetic acid and 1.34 ml concentrated HCl was heated at 45°–50° C. for 2 hours. After cooling the solution to 20° C., 9.09 g dimethyl cis-piperdine-2,5-dicarboxylate was added and stirring was continued for an additional 30 minutes at 20°–25° C. The resulting light orange solution was treated with the portionwise addition of 12.08 g (57 mmol) $Na(OAc)_3BH$ over 30 minutes and stirred for an additional 30 minutes at 30°–35° C. The solution was cooled to 20° C. and diluted with 120 ml $H_2O$ and 120 ml $CH_2Cl_2$ with 36 ml EtOH, followed by the addition of 100 ml hexanes, resulted in the crystallization of a solid which was allowed to granulate overnight at 20°–25° C. Filtration and drying of this solid provided 13.5 g (79.4%) of present title product as a solid melting at 97°–100° C.

Method B

A stirred mixture of 70 ml of $CH_2Cl_2$, 9.8 g (51 mmol) of N-(2-hydroxyethyl)phthalimide and 6.1 ml (0.52 mmol) of 2,6-lutidine was cooled to –4° C. Maintaining the temperature below 15° C., trifluoromethane sulfonic anhydride (8.9 ml, 0.53 mmol) was added slowly over 1 hour. The resulting mixture was stirred at 15°–20° C. for 1.25 hours, then washed sequentially with 40 ml $H_2O$, 40 ml 2N HCl and 40 ml $H_2O$ to yield a solution of N-((2-triflyloxy)ethyl) phthalimide. At 20°–25° C., a separate reaction vessel was charge with 50 ml $CH_2Cl_2$, 55 ml $H_2O$ and 10.6 g (0.1 mol) $Na_2CO_3$. After stirring for 15 minutes, dimethyl cis-piperidine-2,5-dicarboxylate (11.9 g, 50 mmol) and the above reagent solution were added, and the mixture stirred for 1.25 hours at 20°–25° C. The organic layer was separated, washed with 30 ml of water, and the $CH_2Cl_2$ displaced by boiling with hexane to a final volume of 125 ml, during which time the present title product began to crystallize. After stirring and granulating for 1 hour at 0°–5° C., the present title product, 16.7 g, was recovered by filtration; m.p. 98°–100° C.

Method C

To a well-stirred bi-phasic mixture consisting of sodium carbonate (500 g, 4.72 mol) in water (3 liters) and cis-2,5-piperdine dicarboxylate dimethyl ester (240 g, 1.18 mol) in methylene chloride (4.5 liters), a solution of 2(phthalimido) ethyl triflate (417 g, 1.29 mol) in methylene chloride (3 liters) is added in a steady stream over a 3 hour period. The organic layer is separated, and the aqueous layer is extracted with fresh methylene chloride (3 liters). The combined organic extracts are washed with water (3 liters), then with brine (3 liters), dried with anhydrous magnesium sulfate and finally concentrated in vacuo to a solid. The entire residue is triturated in refluxing ether (3 liters) with vigorous stirring for 15 minutes. After cooling to ambient temperature, the solution is poured into hexanes (3 liters), and the resulting mixture is stirred for 18 hours. The present title product is collected by filtration.

PREPARATION 2

Racemic Methyl (7S*,9a S*)-4,6,7,8,9,9a-Hexahydro- 2H,3H-pyrido[1,2-a]pyrazin-1-one-7-carboxylate A mixture of 240 ml of methanol, 16.6 g (44 mmol) of the title product of Preparation 1, and 5.74 ml (97 mmol) of 54% hydrazine was stirred at 20°–25° C. for 17 hours. The mixture was then diluted with 200 ml of $CH_2Cl_2$, granulated for 1 hour, and by-product recovered by filtration with 75 ml $CH_2Cl_2$ wash. The combined filtrate and wash liquor was concentrated to 225 ml by distillation and $CH_2Cl_2$/methanol displaced with isopropyl alcohol by distillation to a final volume of 200 ml. After cooling slowly from 50° C. to 8° C. over a 2 hour period, title product, 9.2 g, was recovered by filtration. The entire batch was purified by recrystallization from $CH_2Cl_2$ to yield 7.45 g of purified title product, identical with the product of Preparation 4 of above cited Bright et al., WO90/08144.

PREPARATION 3 cis-7-Hydroxymethyl-2,3,4,6,7,8,9,9a-octahydro-1H-pyrido[1,2-a]pyrazine

A flame-dried flask fitted with a magnetic stirrer, condenser, and nitrogen inlet was charged with a slurry of lithium aluminum hydride (14.88 g, 0.46 mol) in 500 ml of dry tetrahydrofuran. Title product of the preceding Preparation (53.61 g, 0.25 mol) was added portionwise, in solid form, to the well-stirred mixture over a one hour period. The mixture was then refluxed under nitrogen for 18 hours. After cooling to 15° C., the reaction was quenched by cautious dropwise addition of water (100 ml). The mixture was then filtered, and the filter cake was washed with 150 ml of tetrahydrofuran. The filtrate was concentrated in vacuo to a solid, which was extracted three times with one liter portions of methylene chloride. The tetrahydrofuran and methylene chloride extracts were concentrated in vacuo to afford the title compound (42.06 g, 97.8% yield) as an amorphous solid. HRMS 170.1413, calcd. 170.1419.

$^{13}$C-NMR (300 MHz, CDCl$_3$) delta 65.6, 62.6, 57.8, 56.0, 51.8, 45.8, 34.7, 26.4, 26.0

PREPARATION 4

8-[2-[7S-(2-(3-(1,2-benzisoxazolyl)-2,3,4,6,7,8,9, (9aS-octahydro-1H-pyrido[1,2-a]pyrazinyl)]-ethyl]-8-azaspiro[4.5]-decane-7,9-dione

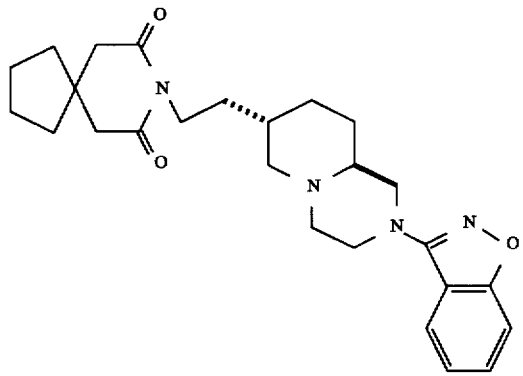

The (−)-amine (0.35 g, 1.17 mmol) from Example 20 and 4,4-tetramethylene glutaric anhydride (0.208 g, 1.24 mmol) were refluxed in toluene for 1 hour. Acetic anhydride (1 ml) was added at this point and heating was continued for two hours. The reaction was cooled to room temperature and diluted with ethyl acetate. This was washed with sodium carbonate solution, with brine and dried over $MgSO_4$. The organic solvents were removed in vacuo and the residue was crystallized from isopropanol (10 ml) to afford the title compound, 0.39, 57% yield. mp 153°–5.5° C; $[\alpha]_D$ −4.1° (c=0.536, $CH_2Cl_2$).

I claim:

1. A process for preparing a substantially optically pure compound of the formula

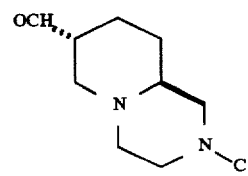

having (7R,9aS-Trans) configuration wherein C is selected from the group consisting of

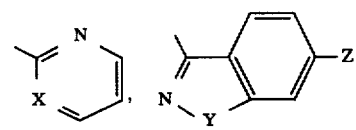

and a nitrogen protecting group which is removable by hydrogenation or acid treatment; wherein X is N or CH; Y is O or S and Z is H or Cl; comprising:

(a) reacting an activated form of C with a racemic compound of the formula

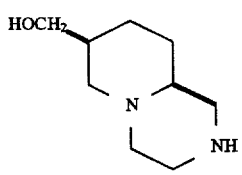

in a reaction inert solvent with an acid acceptor to form a racemic product which has formula

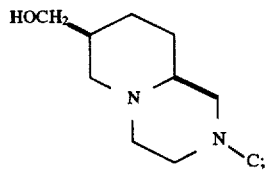

(b) reacting the racemic product of step (a) with a slight molar excess of D-(−)-tartaric acid in a reaction inert solvent forming two diastereomeric salts;

(c) separating the diastereomeric salts of step (b) and treating the salt having (7S,9as-Cis) configuration with base to obtain a compound which has the formula

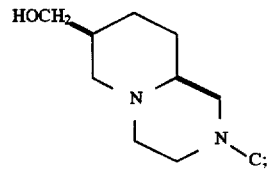

having (7S,9aS-Cis) configuration;

(d) oxidizing the product of step (c) to form a product of the formula

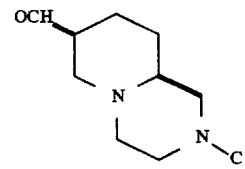

having (7S,9aS-Cis) configuration.

(e) Isomerizing the product of step (d) to produce a compound of the formula

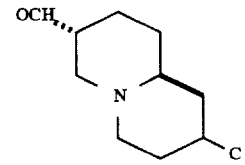

having (7R,9aS-Trans) configuration.

2. A process for preparing a substantially optically pure compound of the formula

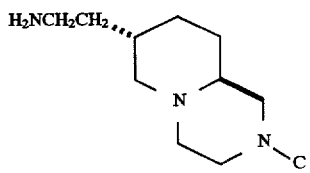

having (7S,9aS-Trans) configuration where in C is selected from the group consisting of H,

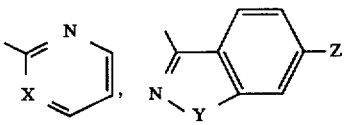

and a nitrogen protecting group which is removable by treatment with a strong acid; wherein X is N or CH; Y is O or S; and Z is H or Cl comprising:

(a) isomerizing a compound of the formula

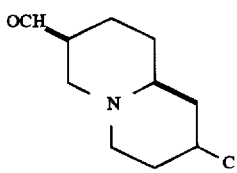

having (7S,9aS-Cis) configuration wherein C is selected from the group consisting of

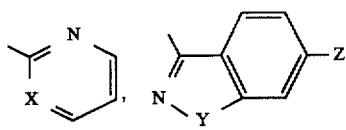

and a nitrogen protecting group removable by treatment with strong acid; wherein X is N or CH; Y is O or S and Z is H or Cl; thereby converting said compound to the (7R,9aS-Trans) configuration; and without isolation adding excess nitromethane and stirring until the reaction is complete to obtain a compound having the formula

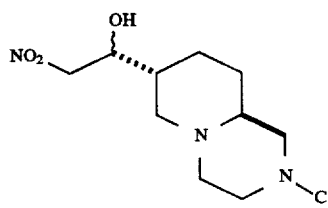

having (7R,9aS-Trans) configuration;

(b) reacting the product of step (a) with an acid anhydride and a weak organic base in a reaction inert solvent to produce a compound having the formula

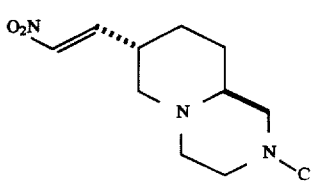

with a (7S,9aS-Trans) configuration;

(c) reducing the compound of step (b) to produce a compound having the formula

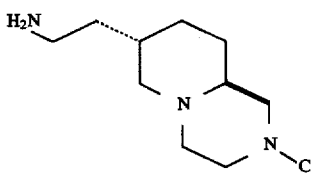

with a (7S,9aS-Trans) configuration; wherein C is selected from the group consisting of

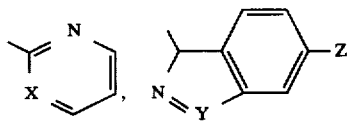

and a nitrogen protecting group which is removable by treatment with a strong acid, wherein X is NH or CH; Y is O or S; and Z is H or Cl;

(d) reacting the product of step (c) wherein C is an amine protecting group which is removable with strong acid, with strong acid in a reaction inert solvent and neutralized with base producing a product having the formula

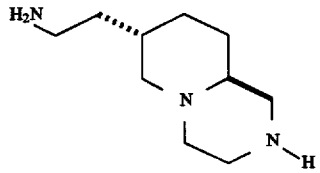

with a (7S,9aS-Trans) configuration.

3. A process for preparing a substantially optically pure compound of the formula

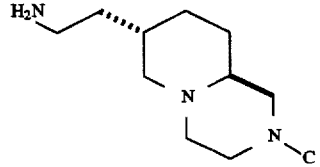

having (7S,9aS-Trans) configuration where in C is selected from the group consisting of H,

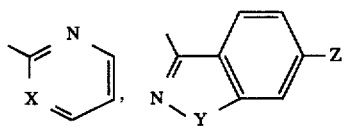

and a nitrogen protecting group which is removable by treatment with a strong acid; wherein X is N or CH; Y is O or S; and Z is H or Cl; comprising:

(a) reacting a compound of the formula

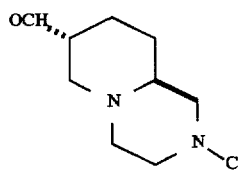

having (7R, 9aS-Trans) configuration wherein C is selected from the group consisting of

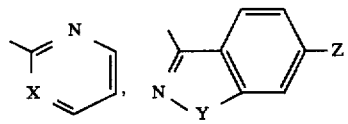

and a nitrogen protecting group removable by treatment with strong acid; wherein X is N or CH; Y is O or S and Z is H or Cl; with a reducing agent to produce a compound of the formula

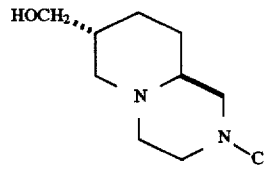

having (7R,9aS-Trans) configuration;

(b) reacting the product of step (a) with a ($C_1$–$C_6$)alkyl, phenyl or alkyl substituted phenyl sulfonyl chloride in a reaction inert solvent and in the presence of a base to form a compound of the formula

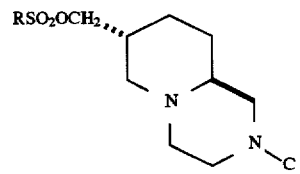

having (7R,9aS-Trans) configuration; wherein R is ($C_1$–$C_6$)alkyl, phenyl or alkyl substituted phenyl (c) reacting the product of step (b) with an alkali metal cyanide in a reaction inert solvent to form a compound of the formula

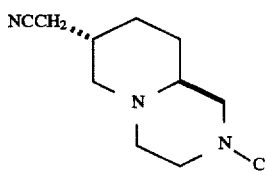

having (7S,9aS-Trans) configuration;

(d) reducing the product of step (c) to form a compound of the formula

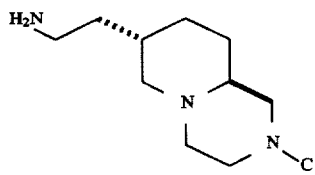

with a (7S,9aS-Trans) configuration; wherein C is selected from the group consisting of

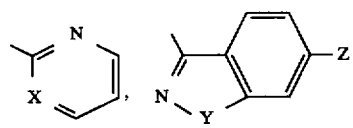

and a nitrogen protecting group which is removable by treatment with a strong acid, wherein X is NH or CH; Y is O or S; and Z is H or Cl;

(e) reacting the product of step (d) wherein C is an amine protecting group which is removable with strong acid, with strong acid in a reaction inert solvent and neutralizing with base to produce a compound having the formula

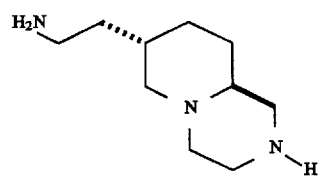

with a (7S,9aS-Trans) configuration.

4. (7S,9aS)-Cis-7-hydroxymethyl-2-(1,2-benzisoxazol-3-yl)- 2,3,4,6,7,8,9,9a-octahydro-1H-pyrido[1,2-a]pyrazine or a pharmaceutically acceptable acid addition salt thereof.

5. A compound selected from the group consisting of (7S,9aS)-Cis-7-formyl-2-(1,2-benzisoxazol-3-yl) -2,3,4,6,7, 8,9,9a-octahydro-1H-pyrido [1,2-a]pyrazine; (7R, 9aS) -Trans-7-formyl-2-(1,2-benzisoxazol-3-yl) -2,3,4,6,7,8,9, 9a-octahydro-1H-pyrido [1,2-a]pyrazine; (7R, 9aS) -Trans-7-(1-hydroxy-2-nitroethyl)-2-(1,2-benzisoxazol-3-yl) -2,3, 4,6,7,8,9,9a-octahydro-1H-pyrido [1,2-a]pyrazine; (7S, 9aS) -Trans-7-(2-nitroethylenyl)-2-(1,2-benzisoxazol-3-yl) -2,3,4,6,7,8,9,9a-octahydro-1H-pyrido [1,2-a]pyrazine; (7S, 9aS) -Cis-7-formyl-2-(tert-butoxycarbonyl)-2,3,4,6,7,8,9, 9a-octahydro-1H-pyrido[1,2-a]pyrazine; (7R,9aS)-Trans-7-formyl-2-(tert-butoxycarbonyl) -2,3,4,6,7,8,9,9a-octahydro-1H-pyrido[1,2-a]pyrazine; (7R,9aS)-Trans-7-(1-hydroxy-2-nitroethyl)-2-(tert-butoxycarbonyl)-2,3,4,6,7,8,9,9a-octahydro-1H-pyrido[1,2-a]pyrazine; (7S,9aS)-Trans-7-(2-nitroethylenyl)-2-(tert-butoxycarbonyl)-2,3,4,6,7,8,9,9a-octahydro-1H-pyrido[1,2-a]pyrazine; and the pharmaceutically acceptable acid addition salts of the foregoing compounds.

6. (7R,9aS)-Trans-7-hydroxymethyl-2-(1,2-benzisoxazol-3-yl)-2,3,4,6,7,8,9,9a-octahydro-1H-pyrido[1, 2-a]pyrazine or a pharmaceutically acceptable acid addition salt thereof.

7. (7R,9aS)-Trans-7-methanesulfonyloxymethyl-2-(1,2-benzisoxazol-3-yl)-2,3,4,6,7,8,9,9a-octahydro-1H-pyrido[1, 2-a]pyrazine or a pharmaceutically acceptable acid addition salt thereof.

8. (7R, 9aS)-Trans-7-cyanomethyl-2-(1,2-benzisoxazol-3-yl)- 2,3,4,6,7,8,9,9a-octahydro-1H-pyrido[1,2-a]pyrazine or a pharmaceutically acceptable acid addition salt thereof.

9. (7S,9aS)-Cis-7-hydroxymethyl-2-(tert-butoxycarbonyl)-2,3,4,6,7,8,9,9a-octahydro-1H-pyrido[1,2-a]pyrazine or a pharmaceutically acceptable acid addition salt thereof.

10. (7R,9aS)-Trans-7-(hydroxymethyl)-2-(tert-butoxycarbonyl)-2,3,4,6,7,8,9,9a-octahydro-1H-pyrido[1,2-a]pyrazine or a pharmaceutically acceptable acid addition salt thereof.

* * * * *